(12) United States Patent
Ye et al.

(10) Patent No.: US 6,833,443 B1
(45) Date of Patent: Dec. 21, 2004

(54) GYMNEMIC ACID DERIVATIVES, PROCESS FOR THE PREPARATION THEREOF AND USE THEREOF AS MEDICINE

(75) Inventors: Wencai Ye, Nanjing (CN); Yue Dai, Nanjing (CN); Xiaodong Cong, Nanjing (CN); Xingxiang Zhu, Nanjing (CN); Shouxun Zhao, Nanjing (CN)

(73) Assignee: Guilin Jiqi Pharmaceutical Co., Ltd., Guangxi (CN)

( * ) Notice: Subject to any disclaimer, the term of this patent is extended or adjusted under 35 U.S.C. 154(b) by 0 days.

(21) Appl. No.: 09/913,322
(22) PCT Filed: Jan. 21, 2000
(86) PCT No.: PCT/CN00/00010
§ 371 (c)(1),
(2), (4) Date: Jan. 15, 2002
(87) PCT Pub. No.: WO00/47594
PCT Pub. Date: Aug. 17, 2000

(30) Foreign Application Priority Data

| Feb. 11, 1999 | (CN) | 99100721 A |
| Feb. 11, 1999 | (CN) | 99100722 A |
| Mar. 12, 1999 | (CN) | 99102823 A |
| Apr. 5, 1999 | (CN) | 99103588 A |

(51) Int. Cl.$^7$ ............................................. C07H 15/00
(52) U.S. Cl. .................... 536/5; 514/26; 514/27; 514/33
(58) Field of Search .................. 514/26, 27, 33; 536/5

(56) References Cited

U.S. PATENT DOCUMENTS 5,843,909 A    12/1998    Atsuchi et al.

FOREIGN PATENT DOCUMENTS

| EP | 0 406 516 A1 | 1/1991 |
| JP | 08040912 | 2/1996 |

OTHER PUBLICATIONS

Yoshikawa et al., *Chem. Pharm. Bull.*, vol. 44, No. 10, pp. 1923–1927 (1996).

Yoshikawa et al., *Chem. Pharm. Bull*, vol. 45, No. 12, pp. 2034–2038 (1997).

Yoshikawa et al., *Chem. Pharm, Bull*, vol. 45, No. 3, pp. 1300–1305 (1997).

Masuda et al., *Biol. Pharm. Bull.*, vol. 19, No. 2, pp. 315–317 (1996).

Tan et al., *Phytochemistry*, vol. 52, pp. 153–192 (1999).

Kazuko Yoshikawa et al., Gymnemic Acid V, VI and VII From Gur–Ma, The Leaves Of Gymnema Sylvestre R. Br., Chem. Pharm. Bull. 37(3)852–854 (1989).

Morihiko Maeda et al., Studies on Taste Modifiers. II. Purification and Structure Determination of Gymnemic Acids, Antisweet Active Principle from Gymnema Sylvestrre Leaves, Tetrahedron Letters, vol. 30, No. 12, pp. 1547–1550, 1989.

*Primary Examiner*—James O. Wilson
*Assistant Examiner*—Ganapathy Krishnan
(74) *Attorney, Agent, or Firm*—Birch, Stewart, Kolasch & Birch, LLP

(57) ABSTRACT

This invention relates to new Gymnemic acid derivatives, their preparation, pharmaceutical composition or extract which contains them, and their medical use, especially the use in the prevention or treatment of the diseases associated with hyperglycemia, hyperlipidemia and platelets aggregation.

13 Claims, No Drawings

GYMNEMIC ACID DERIVATIVES, PROCESS FOR THE PREPARATION THEREOF AND USE THEREOF AS MEDICINE

This application is the national phase under 35 U.S.C. § 371 of PCT International Application No. PCT/CN00/00010 which has an International filing date of Jan. 21, 2000, which designated the United States of America and was not published in English.

1. Field of the Invention

This invention relates to new Gymnemic acid derivatives, their preparation, pharmaceutical composition or extract which contains them, and their medical use, especially the use in the prevention or treatment of the diseases associated with hyperglycemia, hyperlipidemia and platelets aggregation.

2. Background of the Related Art

A lot of studies on Gymnemic Acid derivatives have been done and all of these Gymnemic acid derivatives are from the plant called Gymnema cane, which is classified as Gymnema sylvestre. R. Br. In India, it has been used to treat swelling, snake venom toxin, malaria, as a diuretic or to lower blood sugar level. Yet the Gymnemic acid derivatives and their biological activity mentioned in this invention haven't been reported up to this date.

SUMMARY OF THE INVENTION

The object of this invention is to find new Gymnemic acid derivatives and develop their medical use.

The inventors have found out new Gymnemic acid derivatives of formula I or II and also their medical use, especially in treating hyperglycemia, hyperlipidemia and platelets aggregation. The invention is now performed based on the discovery mentioned above.

In the first part, this invention concerns Gymnemic Acid derivatives formula I or II,

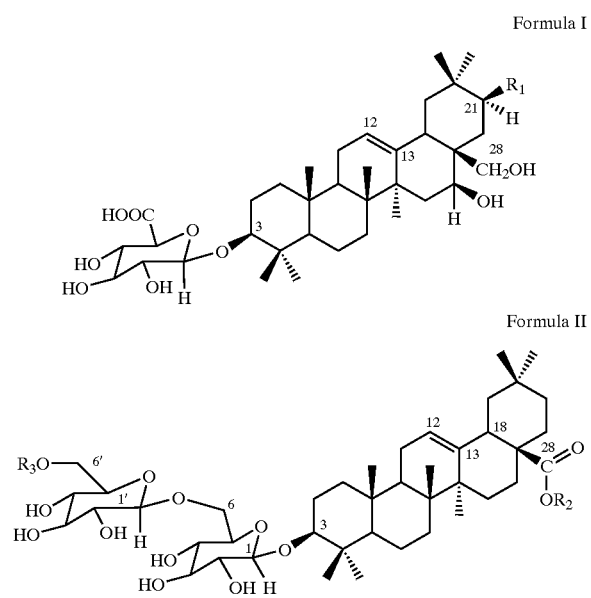

Formula I

Formula II wherein, $R_1$ is H or the radical represented by the following formula

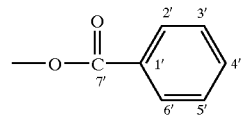

$R_3$ is H, and $R_2$ symbolizes the following radical,

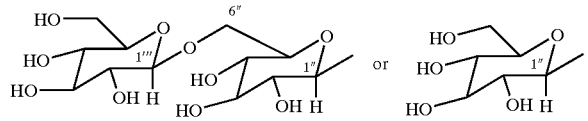

or $R_3$ symbolizes the following radical,

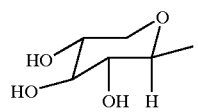

and $R_2$ is H or the following radical,

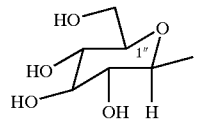

or a pharmaceutical base addition salt thereof.

The second part of this invention relates to pharmaceutical composition which contains at least one kind of Gymnemic Acid derivative of formula I and/or II or pharmaceutical base addition salt thereof as active ingredient, pharmaceutical carrier and excipient.

The third part of the invention involves Gymnemic Acid extract 12.5–40 wt % of which is Gymnemic Acid derivative of formula 1 and/or II.

Another part of this invention relates to pharmaceutical composition for the prevention or treatment of the diseases associated with hyperglycemia, hyperlipidemia and platelets aggregation, which contains at least one kind of gymnemic acid derivative of formula I and/or II or pharmaceutical base addition salt thereof as an active ingredient, pharmaceutical carrier and excipient.

Another part of the invention relates to a pharmaceutical composition for the prevention or treatment of diabetes, which includes at least one kind of Gymnemic Acid derivative of formula I and/or II or pharmaceutical base addition salt thereof as an active ingredient, a pharmaceutical carrier and an excipient.

Another part of this invention relates to a pharmaceutical composition for the prevention or treatment of higher blood lipid level, which contains at least one kind of gymnemic acid derivative of formula I and/or II or a pharmaceutical base addition salt thereof as an active ingredient, pharmaceutical carrier and an excipient.

Another part of this invention relates to pharmaceutical composition for the prevention or treatment of platelets aggregation, which contains at least one kind of gymnemic acid derivative of formula I and/or II or pharmaceutical base addition salt thereof as an active ingredient, pharmaceutical carrier and excipient.

Another part of this invention relates to the preparation of Gymnemic Acid derivative of formula I and If or pharmaceutical base addition salt thereof, which includes the following steps:

a) extracting the plant Gymnema cane with ethane under reflux and then concentrating;

b) extracting concentrated liquid in step a) with cyclohexane, then extracting with n-butanol, concentrating to dryness under reduced pressure, and then obtaining a paste;

c) subjecting the paste in step b) to silica column chromatography with chloroform:methanol=90:10–50:5 or 90:10–60:40 (v/v) as elute, obtaining gymnemic acid derivative of formula I and residue;

d) subjecting the residue in step c) to $C_{18}$ column chromatography with methanol/water=20/80–40/60 (v/v) as eluant, obtaining gymnemic acid derivative of formula II;

e) if desired, converting the obtained gymnemic acid derivative of formula I or II into pharmaceutical base addition salt with an inorganic or organic base.

Another part of this invention relates to a method of preparation of the extract containing Gymnemic Acid derivative of formula I and II which ranges from 12.5–40 wt %, which includes the following steps:

a) extracting Gymnema cane leaves with 60–95% ethanol and concentrating, b) extracting concentrated liquid in step a) with cyclohexane, then extracting with n-butanol, and then concentrating the extract under reduced pressure.

Another aspect of the invention relates to use of Gymnemic Acid derivative of formula I and II or the extract containing Gymnemic Acid derivative of formula I and II for the manufacture of medicament for the prevention or treatment of the diseases and conditions associated with hyperglycemia, hyperlipidemia and platelets aggregation.

Finally, this invention relates to the method of preventing or treating the diseases and conditions associated with hyperglycemia, hyperlipidemia and platelets aggregation, which includes administrating a prophylactic or effective quantity of Gymnemic Acid derivative of formula I and II to a patient suffering from diseases or conditions associated with hyperglycemia, hyperlipidemia and platelets aggregation.

The term "patient" in the invention refers to a mammal, including a human being, and especially a human being.

DETAILED DESCRIPTION OF THE INVENTION

This invention relates to Gymnemic Acid derivative of formula I and II,

Formula I

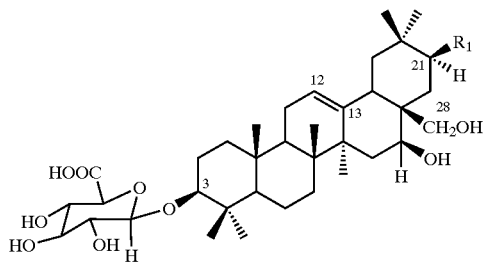

Formula II

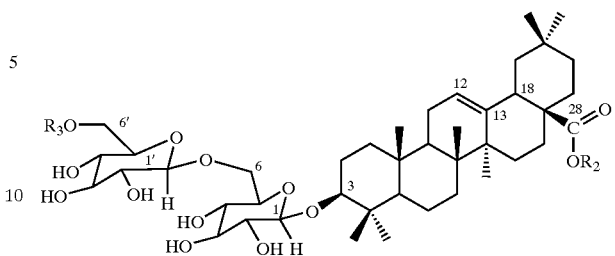

wherein, $R_1$ is H or the radical represented by the following formula

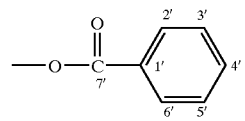

$R_3$ is H, and $R_2$ is the following group,

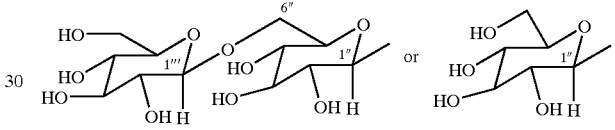

or $R_3$ is the following group,

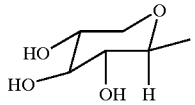

and $R_2$ is H or the following group,

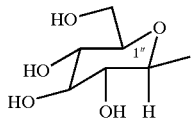

or the pharmaceutical base addition salt.

According to the invention, the pharmaceutical base addition salt of Gymnemic acid of formula I or II includes a salt formed with pharmaceutical inorganic or organic base. The inorganic base, for example, includes alkali or alkali earth metal hydroxide, alkali metal or alkali earth metal carbonate or bicarbonate, alkali metal may be selected from Li, Na, K, alkali earth metal may be selected from Ba, Mg, Ca etc. The organic base, for example, may be triethyl amine etc.

According to this invention, the Gymnemic acid compound preferably is a

According to the invention, the Gymnemic acid compound is preferably a Gymnemic Acid compound of formula I wherein $R_1$ is the following radical.

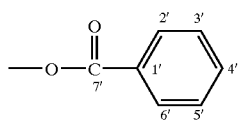

According to the invention, the Gymnemic acid compound is preferably a Gymnemic Acid compound of formula II wherein $R_3$ is H and $R_2$ is the following radical.

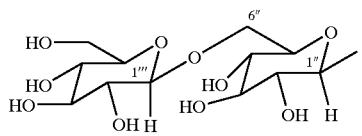

According to the invention, the Gymnemic acid compound is preferably a Gymnemic Acid compound of formula II wherein $R_3$ is H and $R_2$ is the following radical.

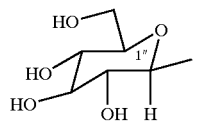

According to the present invention, the Gymnemic acid compound is preferably a Gymnemic Acid compound of formula II wherein $R_3$ is the following radical and $R_2$ is H.

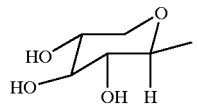

According to the invention, the Gymnemic acid compound is preferably Gymnemic Acid compound of formula II wherein both $R_3$ and $R_2$ are the following radicals respectively.

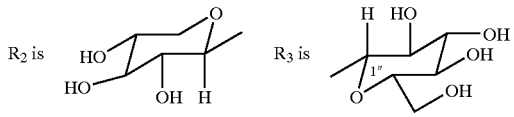

According to the invention, the pharmaceutical composition contains at least one kind of Gymnemic Acid derivative of formula I and/or II, a pharmaceutical carrier and an excipient. For example, the pharmaceutical composition may include, for example, 1.25–2.10 wt % compound A, 0.89–1.5 wt % compound B, 2.40–3.80 wt % compound C, 2.10–3.40 wt % compound D, 2.74–4.60 wt % compound E, and 3.24–5.4 wt % compound F (compounds A, B, C, D, E and F as defined in examples below.). This pharmaceutical composition can be. administrated by gastrointestinal, parenteral or topical administration, such as oral, muscle, subcutaneous, peritoneum, vein etc. The forms of the drug suitable for gastrointestinal administration are for example tablet, capsule, solution, suspension, powder, granules, etc. The forms of the drug suitable for parenteral include injection solution, freeze-dried powder for injection preparations, etc. The drug forms suitable for the topical use are for example, an ointment, cream, paste, patch, and spray. Of all these forms, oral administration is preferred, and a capsule is the preferred be oral form. The pharmaceutical carrier or excipient of the pharmaceutical composition includes binding agent, filling material, wetting agent, disintegrating agent, surfactant, lubricating agent, diluting agent, etc. If desired, a coloring agent, flavoring agent, solubilizer, buffer, etc are also used. The diluting agents in the invention include starch, dextrin, lactose, microcrystalline cellulose, silica gel, etc. Silica gel is preferred. The wetting agents includes water and ethanol. Lubricating agents include talcum powder, and magnesium stearate.

The pharmaceutical composition in the present invention can be produced by the known methods in this art. For example, by mixing Gymnemic Acid derivative of formula I and/or II or pharmaceutical base addition salt with pharmaceutical carrier and excipient.

The dose of Gymnemic Acid derivative of formula I and II depends on many factors such as the character and seriousness level of the disease to be prevented or treated, sex, age, weight, individual response, specific compound, administration route and times of administration. Generally the specific dose depends on the judgment of the physician. Generally speaking, the dosage of the pharmaceutical composition Gymnemic Acid derivative of formula I and II can be in the form of single dose and taken 1–4 times per day.

According to this invention, the derivative or pharmaceutical base addition salt of formula I Gymnemic Acid can be prepared as follows:

a) crushing dry leaves of Gymnema cane, then extracting three times with 60–95% ethanol under reflux, two hours for each, combining extracted liquid and concentrating under reduced pressure until there was no ethanol;

b) extracting the concentrated mixtures in step a) for 3 to 6 times with cyclohexane, then extracting with n-butanol, concentrating to dryness under reduced pressure, obtaining dry extract;

c) subjecting the dry extracts in step b) to silica gel column chromatography with a mixture of chloroform and methanol at a ratio of 90:10 to 60:40 (v/v) as eluant, and obtaining derivatives of formula I, d) If desired, converting the derivative of formula I in step c) into pharmaceutical base addition salt thereof.

According to this invention, the gymnemic acid derivative of formula II can be prepared as follows:

a) Crushing dry leaves of Gymnemacane, then extracting three times with 60–95% ethanol under reflux, two hours for each, combining extracted liquid and concentrating under reduced pressure until there was no ethanol;

b) extracting concentrated mixtures for 3 to 6 times with cyclohexane, then extracting with n-butanol; concentrating to dryness under reduced pressure;

c) mixing the dry extracts in step b) with rough silica gel; subjecting separation with thin layer chromatography of silica gel H with a mixture of chloroform and methanol at a ratio of 90:10 to 50:50 (v:v) as eluant, subjecting the residue after elution to $C_{18}$ column chromatography with the eluant being methanol/water (20:80–40:60), and obtaining a derivative of formula II;

d) if desired, converting the derivative of formula II in step c) into the pharmaceutical base addition salt thereof.

According to this invention, the extract products with 12.5–40 wt % Gymnemic Acid derivative of formula I and formula II can be prepared as follows: raw powder of Gymnema cane leaves were refluxed 1–4 times with 60–95% ethanol, the amount of solvent for each is 6 ml/g, and the extraction time is 1–3 hours. The extract mixtures were combined together and distilled under reduced pressure till there was no ethanol, the concentrated mixture was extlacted with cyclohexane for 1–3 times, 500 ml of solvent was used each time. Then the mixture was extracted for 1–3 times with 500 ml n-butanol, all the extract mixtures were combined and distilled under reduced pressure to obtain the desired product.

This invention gives a faster illustration by the preparation examples and biological activity experiment, but it does not infer any limitation to the invention.

EXAMPLE 1

Preparation of compound A (Gymnemic Acid derivative of formula I wherein the $R_1$ being H) and compound B (Gymnemic Acid derivative of formula I wherein the $R_1$ being group as follow)

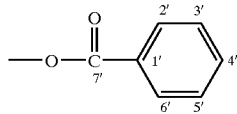

Gymnema cane leaves (1000 g raw powder) were extracted under reflux 3 times with 60% ethanol. Six liters of solvent were used for each extraction, and each extraction lasted for 2 hours. The extract mixtures were combined and distilled under reduced pressure until there was no ethanol, the concentrated mixture was extracted with 0.5 L cyclohexane and butane for 3 times. All the n-butane extract mixtures were combined and distilled under reduced pressure to obtain 64.0 g dry extract product. The dry extract (32.0 g) was added into 60 g of 60–100 mesh rough silica gel, and the mixture was vaporized to dryness on a water pan. 450 g 200–300 mesh (m) silica gel was loaded into a column by a wet method, and then the treated sample was added. Column separation was performed using 90:10–60:40 (v:v) mixtures of chloroform-methanol as eluant. 80 mg of compound A and 60 mg of compound B were obtained.

The physical and spectral data of compound A and compound B were as follows:

Compound A

Amorphous powder: mp 198–202° C.; $[\alpha]_{20}^D$+16.0° (c0.10, MeOH);

IR $\nu_{max}$ 3414 (OH), 1724 (COOH), 1636 (C=C), 1458, 1380, 1054 cm$^{-1}$;

$^1$HNMR (500 MHz, pyridine—d5) δ 0.86 (3H, s, Me), 0.95 (3H, s, Me), 1.01 (9H, s, 3×Me), 1.32 (3H, s, Me), 1.39 (3H, s, Me), 3.39 (1H, dd, J=4.3 and 11.8 Hz, H-3α), 3.68 (1H, d, J=10.5 Hz, H-28a), 4.43 (1H, d, J=10.5 Hz, H-28b), 4.68 (1H, m, H-16α), 5.04 (1H, d, J=7.8 Hz, H-1 of glucouronic acid), 5.26 (1H, brs, H-12); $^{13}$CNMR (125 MHz, pyridine-d5), See Tables 1 and 2; FAB MS m/z 657 [M+Na]$^+$.

Compound B

Amorphous; mp 192–195° C.; $[\alpha]_{20}^D$+27.2° (c 0.15, MeOH);

IR $\nu_{max}$ 3444 (OH), 1724, 1700, 1635 (C=C), 1457, 1388, 1280, 1074, 720 cm$^{-1}$; $^1$HNMR (500 MHz, pyridine) δ 0.98 (3H, s, Me), 1.01 (3H, s, Me), 1.02 (9H, s, 3×Me), 1.07 (3H, s, Me), 1.30 (3H, s, Me), 1.34 (3H, s, Me), 1.36 (3H, s, Me), 3.40 (1H, dd, J=4.5 and 12.0 Hz, H-3α), 3.70 (1H, d, J=10.2 Hz, H-28a), 4.42 (1H, d, J=10.2 Hz, H-28b), 4.70 (1H, m, H-16α), 5.10 (1H, d, J=7.8 Hz, H-1 of glucouronic acid), 5.70 (1H, dd, J=4.7 and 12.3 Hz, H-21α), 7.47 (3H, overlap, H-3', -4' and -5'), 8.25 (2H, dd, J=1.4 and 4.8 Hz, H-2' and -6'); $^{13}$CNMR (125 MHz, pyridine-d5), See Tables 1 and 2; FAB MS m/z 777 [M+Na]$^+$.

TABLE 1

$^{13}$CNMR data of glucoside liquid of compound A and B

| Carbon atom | Compound A | Compound B |
| --- | --- | --- |
| 1 | 38.8 | 38.8 |
| 2 | 26.6 | 26.6 |
| 3 | 89.0 | 89.0 |
| 4 | 39.5 | 39.6 |
| 5 | 55.7 | 55.7 |
| 6 | 18.4 | 18.4 |
| 7 | 32.9 | 33.0 |
| 8 | 40.1 | 40.1 |
| 9 | 47.1 | 47.1 |
| 10 | 36.7 | 36.7 |
| 11 | 23.8 | 23.9 |
| 12 | 122.6 | 123.1 |
| 13 | 143.9 | 142.6 |
| 14 | 43.8 | 43.7 |
| 15 | 36.7 | 36.8 |
| 16 | 66.6 | 66.4 |
| 17 | 41.1 | 43.8 |
| 18 | 44.4 | 44.2 |
| 19 | 47.1 | 47.2 |
| 20 | 31.1 | 36.0 |
| 21 | 34.3 | 75.6 |
| 22 | 26.2 | 33.3 |
| 23 | 28.2 | 28.2 |
| 24 | 16.9 | 16.9 |
| 25 | 15.7 | 15.7 |
| 26 | 17.0 | 17.0 |
| 27 | 27.2 | 27.0 |
| 28 | 68.9 | 66.8 |
| 29 | 33.4 | 29.2 |
| 30 | 24.1 | 18.8 |
| Acyl 1' | | 131.6 |
| Acyl 2' | | 129.9 |
| Acyl 3' | | 128.9 |
| Acyl 4' | | 133.2 |
| Acyl 5' | | 128.9 |
| Acyl 6' | | 129.9 |
| Acyl 7' | | 166.3 |

TABLE 2

$^{13}$CNMR data of saccharide part compound A and B

| 3-position substitution | Compound A | Compound B |
| --- | --- | --- |
| Glucouronic acid 1 | 107.3 | 107.3 |
| Glucouronic acid 2 | 75.6 | 75.6 |
| Glucouronic acid 3 | 78.2 | 78.2 |
| Glucouronic acid 4 | 73.5 | 73.6 |
| Glucouronic acid 5 | 77.8 | 77.7 |
| Glucouronic acid 6 | 173.1 | 173.3 |

EXAMPLE 2

Preparation of Compound C (formula II Gymnemic Acid derivative with R₃ as H and R₂ as the following group),

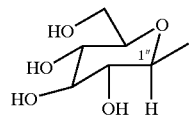

compound D (formula II Gymnemic Acid derivative with R₃ as follows and R₂ as H),

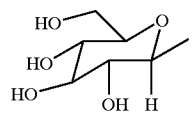

compound E(formula II Gymnemic Acid derivative with R₃ as follows),
R₂ is

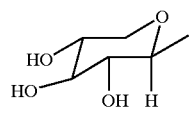

R₃ is

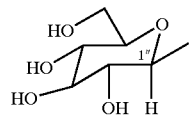

R₂ as follows and compound F(formula II Gymnemic Acid derivative with R₃ as H and R₂ as follows)

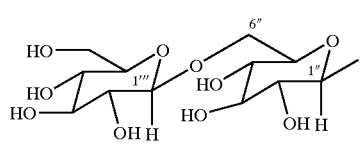

1000 g raw powder of Gymnema cane leaves were refluxed for 3 times with 75% ethanol. 6.0 L solvents were used, 2 hours for each time. The extract mixtures were combined together and distilled under reduced pressure until there was no ethanol, and the condensed mixture was extracted with 0.5 L cyclohexane and butane for 3 times. All the n-butane extract mixtures were gathered and distilled under reduced pressure to obtain 72.0 g dry extract product. 36.0 g dry extract substance was taken and added into 60 g 60–100 mesh rough silica gel, and the mixture was vaporized to dryness on a water pan. 400 g 200–400 mu silica for thin-layer separation were loaded into a column in a wet method, then the treated sample was added to undergo column separation with elution by 90:10–50:50 chloroform-methanol mixtures. 130 mg compound C, 115 mg compound D, 160 mg compound E and 195 mg compound F were obtained respectively.

The physical and spectral data of compound C were as follows:

Amorphous powder; mp 206–209° C.; $[\alpha]_{20}^D$ −16.0° (c 0.11, MeOH ); IR $v_{max}$ 3424 (OH), 1735 (COOR), 1636 (C=C), 1457, 1034 cm⁻¹; ¹HNMR (400 MHz, pyridine-d5) δ 0.82 (3H, S, Me), 0.87 (3H, s, Me), 0.91 (3H, s, Me), 0.97 (3H, s, Me), 1.07 (3H, s, Me), 1.20 (3H, s, Me), 1.23 (3H, s, Me), 3.17 (1H, dd, J=3.5 and 10.2 Hz, H-18), 3.30 (1H, d, J=3.9 and 11.7 Hz, H-3α), 5.37 (1H, brs, H-12), ¹³CNMR (100 MHz, pyridine-d5), See Tables 3 and 4; FAB MS m/z 943 [M+H]⁺.

The physical and spectral data of compound D were as follows:

Amorphous powder; mp 202–204° C.; $[\alpha]_{20}^D$ −3.2° (c 0.15, MeOH); IR $v_{max}$ 3410 (OH), 1710 (COOR), 1638 (C=C), 1458, 1036 cm⁻¹; ¹HNMR (400 MHz, pyridine-d5) δ 0.87 (3H, s, Me), 0.91 (3H, s, Me), 0.96 (3H, a, Me), 1.02 (3H, s, Me), 1.10 (3H, s, Me), 1.24 (3H, S, Me), 1.29 (3H, s, Me), 3.30 (1H, dd, J=4.5 and 11.5 Hz, H -3α), 5.38 (1H, brs, H-12), ¹³CNMR (100 MHz, pyridine-d5), See Tables 3 and 4; FAB MS m/z 935[M+Na]⁺.

The physical and spectral data of compound E were as follows:

Amorphous powder; mp 212–215° C.; [α]20−9.6° (c 0.20, MeOH); IR $v_{max}$ 3414 (OH), 1740 (COOR), 1636 (C=C), 1460, 1364, 1044, 896 cm⁻¹; ¹HNMR (500 MHz, pyridine-d5) δ 0.85 (3H, a, Me), 0.90 (3H, s, Me), 0.94 (3H, s, Me), 1.00 (3H, s, Me), 3.19 (1H, dd, J=4.0 and 13.7 Hz, H-18), 3.32 (1H, d, J=4.4 and 11.7 Hz, H-3 α), 5.40 (1H, brs, H-12), ¹³CNMR (100 MHz, pyridine-d5), see Tables 3 and 4; FAB MS m/z 943 [M+Na]⁺.

The physical and spectral data of compound F were as follows:

Amorphous powder; mp 209–211° C.; [α]20−12.1° (c 0.12, MeOH); IR $v_{max}$ 3424 (OH), 1734 (COOR), 1636 (C=C), 1458, 1047 cm⁻¹; ¹HNMR (400 MHz, pyridine-d5) δ 0.87 (3H, s, Me), 0.90 (3H, s, Me), 0.92 (3H, s, Me), 1.00 (3H, s, Me), 1.09 (3H, s, Me), 1.22 (3H, s, Me), 1.26 (3H, s, Me), 3.20 (1H, dd, J=3.5 and 13.6 Hz, H-18), 3.33 (1H, d, J=4.4 and 11.5 Hz, H-3α), 5.39 (1H, brs, H-12), ¹³CNMR (100 MHz, pyridine-d5), see Tables 3 and 4; FAB MS m/z 1127[M+H]⁺.

TABLE 3

¹³CNMR data of glucoside ligand of compound C–F

| Carbon atom | Compound C | Compound D | Compound E | Compound F |
|---|---|---|---|---|
| 1 | 38.8 | 38.7 | 38.7 | 38.7 |
| 2 | 26.6 | 26.7 | 26.7 | 26.7 |
| 3 | 88.9 | 89.0 | 89.0 | 89.0 |
| 4 | 39.4 | 39.5 | 39.5 | 39.5 |

TABLE 3-continued

$^{13}$CNMR data of glucoside ligand of compound C–F

| Carbon atom | Compound C | Compound D | Compound E | Compound F |
|---|---|---|---|---|
| 5 | 55.7 | 55.8 | 55.8 | 55.8 |
| 6 | 18.4 | 18.3 | 18.5 | 18.5 |
| 7 | 33.0 | 33.1 | 33.1 | 33.1 |
| 8 | 39.8 | 39.9 | 39.9 | 39.9 |
| 9 | 47.9 | 48.0 | 48.0 | 48.0 |
| 10 | 36.9 | 37.0 | 37.0 | 37.0 |
| 11 | 23.7 | 23.7 | 23.8 | 23.7 |
| 12 | 122.9 | 122.8 | 123.0 | 122.9 |
| 13 | 144.0 | 144.4 | 144.0 | 144.1 |
| 14 | 42.0 | 42.1 | 42.1 | 42.1 |
| 15 | 28.2 | 28.2 | 28.2 | 28.2 |
| 16 | 23.3 | 23.4 | 23.4 | 23.4 |
| 17 | 46.9 | 46.5 | 47.0 | 47.0 |
| 18 | 41.6 | 41.9 | 41.7 | 41.7 |
| 19 | 46.2 | 46.1 | 46.2 | 46.3 |
| 20 | 30.7 | 30.9 | 30.8 | 30.8 |
| 21 | 33.9 | 34.4 | 34.0 | 34.0 |
| 22 | 32.5 | 33.1 | 32.5 | 32.5 |
| 23 | 28.1 | 28.2 | 28.2 | 28.3 |
| 24 | 17.0 | 17.0 | 17.0 | 17.0 |
| 25 | 15.5 | 15.8 | 15.6 | 15.6 |
| 26 | 17.4 | 17.3 | 17.5 | 17.5 |
| 27 | 26.0 | 26.1 | 26.1 | 26.1 |
| 28 | 176.4 | 180.2 | 176.5 | 176.5 |
| 29 | 33.1 | 33.2 | 33.2 | 33.2 |
| 30 | 23.6 | 23.7 | 23.7 | 23.7 |

TABLE 4

$^{13}$CNMR data of saccharic part of compound C–F

|  | Compound C | Compound D | Compound E | Compound F |
|---|---|---|---|---|
| 3-position substitution |  |  |  |  |
| Glc1 | 106.9 | 107.0 | 107.0 | 106.9 |
| Glc2 | 75.1 | 75.0 | 75.0 | 75.2 |
| Glc3 | 78.4 | 78.3 | 78.3 | 78.4 |
| Glc4 | 71.6 | 71.5 | 71.5 | 71.5 |
| Glc5 | 77.0 | 77.0 | 77.0 | 77.0 |
| Glc6 | 70.4 | 70.4 | 70.4 | 70.5 |
| Glc'1 | 105.4 | 105.4 | 105.4 | 105.4 |
| Glc'2 | 75.5 | 75.6 | 75.6 | 75.6 |
| Glc'3 | 78.5 | 78.5 | 78.5 | 78.6 |
| Glc'4 | 71.7 | 71.6 | 71.6 | 71.7 |
| Glc'5 | 78.4 | 76.9 | 76.9 | 78.5 |
| Glc'6 | 62.7 | 69.8 | 69.8 | 62.6 |
| Xyl1 |  | 106.0 | 106.0 |  |
| Xyl2 |  | 74.9 | 74.9 |  |
| Xyl3 |  | 78.0 | 78.1 |  |
| Xyl4 |  | 71.1 | 71.1 |  |
| Xyl5 |  | 67.0 | 67.1 |  |
| 28 position substitution |  |  |  |  |
| Glc"1 | 95.7 |  | 95.8 | 95.7 |
| Glc"2 | 74.1 |  | 74.1 | 73.9 |
| Glc"3 | 78.8 |  | 78.9 | 78.7 |
| Glc"4 | 71.0 |  | 71.1 | 70.9 |
| Glc"5 | 79.3 |  | 79.3 | 78.0 |
| Glc"6 | 62.1 |  | 62.2 | 69.3 |
| Glc'''1 |  |  |  | 105.3 |
| Glc'''2 |  |  |  | 75.2 |
| Glc'''3 |  |  |  | 78.5 |
| Glc'''4 |  |  |  | 71.7 |
| Glc'''5 |  |  |  | 78.4 |
| Glc'''6 |  |  |  | 62.7 |

Biological Activity Experiments

EXAMPLE 1

Effect of compound B on increasing blood sugar in rats caused by sucrose

Female SD rats fasted for 24 hours and were randomly divided into several groups. Test groups are given 50, 109, 200 mg/kg compound B, and the positive-control group was given 100 mg/kg performing. The normal group, control group and blank group were given the same amount of water. The given medicine volume was 10 mg/kg, after 30 minutes each group was given saccharose 1/kg(5 ml/kg) except the normal group, and blood was extracted from the eyes of rats after 30, 60 and 120 minutes respectively, the content of glucose in the serum was measured.

The result was, after the rats were given saccharose for 30, 60 minutes, the value of blood sugar increased apparently. The compound B at 200 mg/kg and performing at 100 mg/kg within 30 minutes can both reduce the increased value of blood sugar remarkably, and the strength of the two compounds was similar. See Table 5 for the results.

TABLE 5

The effect of compound B on the increasing blood sugar in rats caused by sucrose
($X \pm SD$, n = 10)

| group | dose (mg/kg) | Value of blood sugar (mmol/L) | | |
|---|---|---|---|---|
|  |  | 30 minutes | 60 minutes | 120 minutes |
| Normal group |  | 3.56 ± 0.64 | 4.12 ± 0.72 | 3.76 ± 0.69 |
| control group |  | 6.58 ± 0.87$^{\triangle\triangle}$ | 5.93 ± 1.27$^{\triangle\triangle}$ | 4.54 ± 1.37 |
| compound B | 50 | 6.03 ± 0.86 | 6.42 ± 0.78 | 4.26 ± 1.03 |
|  | 100 | 5.12 ± 1.29** | 5.77 ± 1.09 | 4.53 ± 0.94 |
|  | 200 | 4.43 ± 0.72** | 4.73 ± 0.83** | 4.07 ± 0.70 |
| phenformin | 100 | 4.24 ± 0.87** | 4.74 ± 0.90* | 4.79 ± 1.03 |

$^{\triangle\triangle}$P < 0.01, compared with normal group;
*P < 0.05, *P < 0.01, compared with control group.

EXAMPLE 2

The effect of compound B on the contents of TG, cholesterol in the serum of hypertipidemia rats.

Male SD rats with a weight of 130–170 g, normal group, was given common food. Other groups were given food having high lipid content (1%cholesterol, 10%lard, 0.3% cholic acid, 0.2% methylthio imidazole and 88.5% common forage, made into a block.). For 14 sequential days, rats fasted for 12 hours were measured by reagent box method to obtain the contents of TG and cholesterol in serum. Then they were divided according to the value of blood fat content into different group. The experimental group was given 50, 100. 200 mg/kg compound B, the positive-control group was given clofibrate 100 mg/kg, and the control group was given water. The given medicine volume was 10 ml/kg, for 10 days, each group was still given high fat forage for 5 days before being given medicine, and common forage was given in the later 5 days. The rats were fasted for 11 hours before being given the final administration and blood of each rat was extracted to obtain the content of TG and cholesterol in serum 1 hour after being given medicine.

The results show that 10 days after rats were given forage having high grease, the contents of TG and cholesterol increased. Compound B 50, 100, 200 mg/kg and clofibrate 100 mg/kg can both reduced the contents of TG and cholesterol in blood serum of hyperlipidemia rats, and compound B 200 mg/kg has the same effect as 100 mg/kg clofibrate in reducing hyperlipidemia, see Table 6.

TABLE 6

The effect of compound B on the contents of blood lipid in hyperlipidemia rats
($X \pm SD$, n = 9–10)

| group | dose (mg/kg) | TG (mmol/L) Before administration | TG (mmol/L) After administration | Total cholesterol (mmol/L) Before administration | Total cholesterol (mmol/L) After administration |
|---|---|---|---|---|---|
| Normal group | | 1.02 ± 0.22 | 1.04 ± 0.15 | 2.43 ± 0.41 | 1.99 ± 0.47 |
| control group | | 2.64 ± 0.82 | 3.04 ± 0.93 | 4.10 ± 0.51 | 4.77 ± 0.63$^{\Delta\Delta}$ |
| compound B | 50 | 2.72 ± 0.61 | 2.41 ± 0.44 | 4.29 ± 0.60 | 3.92 ± 0.58** |
| | 100 | 2.54 ± 0.90 | 1.75 ± 0.53** | 4.02 ± 0.59 | 2.94 ± 0.66** |
| | 200 | 2.72 ± 0.76 | 1.37 ± 0.40** | 4.18 ± 0.61 | 2.31 ± 0.74** |
| clofibrate | 100 | 2.51 ± 0.77 | 2.72 ± 0.74 | 4.33 ± 0.51 | 2.15 ± 0.76** |

$^{\Delta\Delta}P < 0.01$, compared with normal group;
**$P < 0.01$, compared with control group

EXAMPLE 3

Effect of compound B on blood platelet aggregation in rabbits in vitro.

Blood was taken from rabbit heart by puncture, to which was added 3.8% potassium citrate for anticoagulation (1:9). Certification for 15 minute at 1000 rpm takes the upper layer as rich blood platelet plasma (prp), and then centrifugation for 10 minutes with 4000 rpm takes the supernatant as poor blood platelet plasma (ppp). Transfer ppp (200 ul) to a nephelotube, and add into different concentrations of physiological brine solution 10 ul of the compound B. The fugal concentrations are respectively 250, 500, 1000 μg/ml. 10 μl physiological brine of aspirin was added to a positive control tube, then it was put into a measuring cell after warming for 2 minutes at 37° C. 10 ul of physiological brine solution of ADP sodium salt was added with stirring. The final concentration is $1.0 \times 10^5 M$. The maximal aggregation ratio on PAM-1 type of blood platelet instrument was observed within 3 minutes.

The result shows that the compound B 500, 1000 μg/ml and aspirin 250 μg/ml obviously inhibit blood platelet from aggregating.

TABLE 7

Effect of compound B on blood platelet aggregation in rabbit
($X \pm SD$, n = 8)

| Group | Final concentration | Maximal aggregation ratio (%) | Inhibition ratio |
|---|---|---|---|
| Control group | | 47.9 ± 5.2 | |
| compound B | 250 | 43.6 ± 7.0 | 9.0 |
| | 500 | 35.9 ± 4.5** | 25.1 |
| | 1000 | 27.8 ± 4.8** | 42.0 |
| Aspirin | 250 | 23.7 ± 6.0** | 50.3 |

**$P < 0.01$, compared with control group

EXAMPLE 4

Effect of compound F on blood sugar elevation in rat.

Male Kun Ming strain mice are divided into randomly experimental groups, and they respectively took orally the compound F at 50, 100, 2000 mg/kg. The positive control group took orally glybenclamide 50 mg/kg, and the blank control group and normal control group take orally the same distilled water. The volume of medicine given is 20 ml/kg, lasting 7 days. They are forbidden to give feedstuff 10 hours before the last time of administration. Each group is given 2.5 g/kg (10 ml/kg) dextrose solution except of normal control group. Before and after 30 minute of administration of dextrose, 100 ul of blood was sampled from the eyepit, and the content of dextrose in serum was measured by way of dextrose oxygenation enzyme.

Result 30 minutes after mice orally took dextrose, the blood sugar obviously rises. Both the compound F 100, 200 mg/kg and 50 mg/kg inhibits blood sugar in mice from rising. The function of the compound B 200 mg/kg and glybenclamide 500 mg/kg in lowering blood sugar is similar, which may be seen in Table 8.

TABLE 8

| Group | Dose (mg/kg) 0 minute | Value of blood sugar 30 minutes |
|---|---|---|
| Normal Group | | 6.20 ± 1.01 | 6.64 ± 1.04 |
| Control Group | | 6.55 ± 1.16 | 13.94 ± 3.22 |
| compound F | 50 | 6.79 ± 1.16 | 12.01 ± 1.88 |
| | 100 | 6.09 ± 1.34 | 9.59 ± 2.25** |
| | 200 | 6.42 ± 0.99 | 9.16 ± 1.08** |
| glybenclamide | 50 | 4.48 ± 0.83** | 8.18 ± 1.72** |

$P < 0.01$, compared with normal group;
**$p < 0.01$, compared with control group

EXAMPLE 5

Effect of compound F on the content of triglycerides and cholesterol in the serum of hyperlipidemia rat.

Male SD rats weighing 130–170 g were used. The normal group was given general feedstuff, and the other groups were given high-fat (1% cholesterol, 10% pig oil, 0.3% cholic acid, 0.2% methylthio imidazole and 88.5% normal feedstuff are made stuff by oneself). After the feedstuff is run for 14 days and the rats were forbidden to eat for 12 hours, the content of triglycerides and cholesterol in rat's serum was measured. Then, the rats were grouped randomly according to blood lipid value. The experiment group was given compound F (50, 100, 200 mg/kg.), the positive-control group was orally given clofibrate (100 mg/kg), and the control group was given distilled water. The volume of administration was, 10 ml/kg, lasting 10 days. Each group was given high-fat feedstuff in the first 5 days of giving drugs, and then general feedstuff in the next 5 days. Fasting of 11 hours is conducted before the last time of giving drugs. After giving drugs for 1 hour, blood was taken and the content of ester and cholesterol in the blood serum was measured.

Result

The content of TG and cholesterol in the blood serum of rat elevates obviously after given high-fat feedstuff for 10 days. 50 mg/kg, 100 mg/kg, 200 mg/kg of compound F and 200 mg/kg clofibrate make the level of triglycerides and cholesterol in blood serum of rat with high-fat blood diseases lower. The action 200 mg/kg of the compound F is the similar as to that of 100 mg/kg of clofibrate in the function of lowering blood fat. (Table 9)

to a final concentration of 250 $\mu$g/ml. Observe the maximal aggregation ratio on PAM-1 type instrument of blood platelet aggregation within 3 minute.

The result shows that 500, 1000 $\mu$g/ml of the compound F and aspirin 250 $\mu$g/ml obviously inhibit the aggregation of blood platelet.

TABLE 10

The effect of the compound F on aggregation of rabbit's blood platelets in vitro.

| Group | Final concentration ($\mu$g/ml) | Maximal aggregation rate (%) | Inhibition rate (%) |
| --- | --- | --- | --- |
| Control | | 47.9 ± 5.2 | |
| Compound F | 250 | 43.6 ± 7.0 | 9.0 |
| | 500 | 35.9 ± 4.5** | 25.1 |
| | 1000 | 27.8 ± 4.8** | 42.0 |
| Aspirin | 250 | 23.7 ± 6.0** | 50.3 |

**$P < 0.01$ (compared with the control)

EXAMPLE 7

Effect of Compound B on Blood Sugar in Normal Mice.

Male Kun Ming strain mice are divided into random experimental groups, and they respectively take orally the compound B at 50, 100, 2000 mg/kg. The positive control group orally took tolbutol at 100 mg/kg. The blank control group took orally same distilled water. The volume of

TABLE 9

The effect of compound F on the content of blood fat of rat with high-fat blood disease. (X ± SD, n = 9–10)

| Group | dose (mg/kg) | triglycerides (mmol/L) | | Total cholesterin (mmol/L) | |
| --- | --- | --- | --- | --- | --- |
| | | Before administration | After administration | Before administration | After administration |
| Normal group | | 1.02 ± 0.22 | 1.04 ± 0.15 | 2.43 ± 0.41 | 1.99 ± 0.47 |
| Control group | | 2.64 ± 0.82 | 3.04 ± 0.93 | 4.10 ± 4.51 | 4.77 ± 0.63 |
| compound B | 50 | 2.72 ± 0.61 | 2.41 ± 0.44 | 4.29 ± 0.60 | 3.92 ± 0.58** |
| | 100 | 2.54 ± 0.90 | 1.75 ± 0.53** | 4.02 ± 0.59 | 2.94 ± 0.66** |
| | 200 | 2.72 ± 0.76 | 1.37 ± 0.40** | 4.18 ± 0.61 | 2.31 ± 0.74** |
| Clofibrate | 100 | 2.51 ± 0.77 | 2.72 ± 0.74 | 4.33 ± 0.51 | 2.15 ± 0.76** |

$^{\triangle\triangle}P < 0.01$, (compared with normal group);
**$P < 0.01$ (compared with control group)

EXAMPLE 6

Effect of Compound F on Blood Platelet Aggregation in Rabbit

Take blood from rabbit heart by puncturing, add 3.8% of potassium citrate for anticoagulation (1:9), centrifuge for 15 minutes at 1000 rpm, take the upper layer as blood platelet rich plasma (prp), and then centrifuge for 10 minutes at 400 rpm, and take supernatant as blood platelet poor plasma (ppp). The final concentration of compound F is respectively 250, 500, 1000 $\mu$g/ml, and the final concentration is respectively 250, 500, 1000 ug/ml. Add 10 ul of physical brine of aspirin to the positive-control tube to a final concentration of 250 $\mu$g/ml, and add 10 $\mu$l of physical brine to the control tube medicine given is 20 ml/kg, lasting 14 days. The test drug was administered (provided that they are pre-forbidden to give food 5 hrs before administration) after the days 1, 3, 7, 14 of administration. 3 hrs after administration, blood (10 ul) was taken from the eyepit. The content of dextrose in serum was measured by reagent box.

Result

Compound B 50, 100, 200 mg/kg by continuous administration for 14 days has no obvious effect on blood sugar of normal mice, but tolbutol starting from day 3 of administration shows an obvious effect for lowering the blood sugar of normal mice. The result is also seen in Table 11.

TABLE 11

Effect of compound B on blood sugar in normal mice.
($X \pm SD$, n = 10)

| Group | Dose (mg/kg) | Value of blood sugar | | | |
|---|---|---|---|---|---|
| | | 1 | 3 | 7 | 14 (day) |
| control Group | | 5.21 ± 1.10 | 7.10 ± 1.30 | 8.56 ± 0.74 | 7.52 ± 1.29 |
| compound B | 50 | 5.84 ± 0.94 | 7.56 ± 0.92 | 8.51 ± 1.06 | 8.27 ± 0.66 |
| | 100 | 6.48 ± 1.28 | 7.73 ± 2.26 | 8.71 ± 0.97 | 7.45 ± 1.59 |
| | 200 | 6.41 ± 1.04 | 6.28 ± 1.19 | 8.46 ± 0.88 | 7.86 ± 1.56 |
| tolbutol | 100 | 6.48 ± 1.18 | 5.22 ± 0.80** | 6.62 ± 0.96 | 5.75 ± 1.02** |

**$p < 0.05$, compared with control group

What is claimed is:

1. A gymnemic acid derivative of general formula I or formula II,

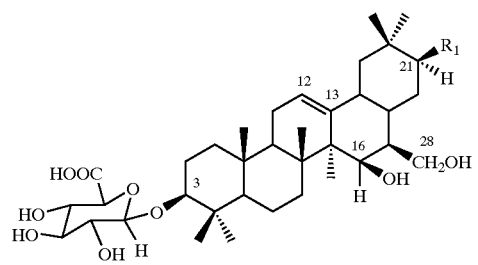

Formula I

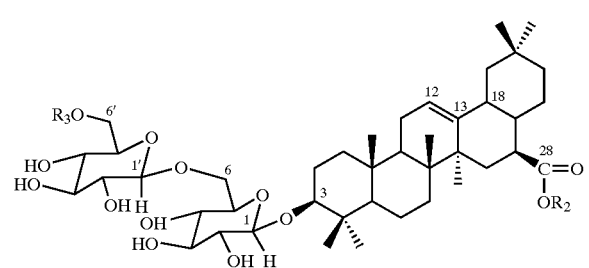

Formula II wherein, $R_1$ is H or the radical represented by the following formula

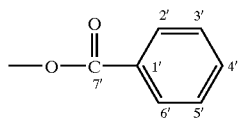

$R_3$ is H, and $R_2$ symbolizes the following radical,

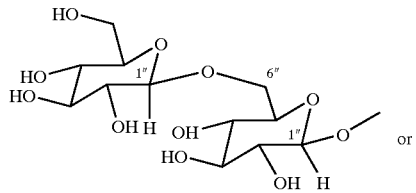

-continued

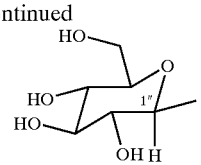

or $R_3$ symbolizes the following radical,

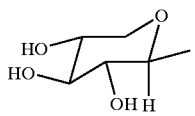

$R_2$ is H or the following radical,

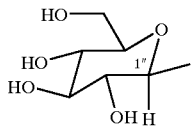

or a pharmaceutically acceptable base addition salt thereof.

2. The gymnemic acid derivative of claim 1, wherein $R_1$ in formula I is hydrogen.

3. The gymnemic acid derivative of claim 1, wherein $R_1$ in formula I is a group of the formula:

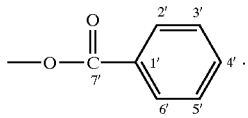

4. The gymnemic acid derivative of claim 1, wherein $R_3$ in formula II is hydrogen, $R_2$ is group of formula:

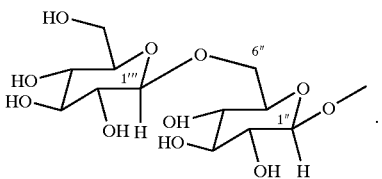

5. The gymnemic acid derivative of claim 1, wherein $R_3$ in formula II is hydrogen, $R_2$ is group of formula:

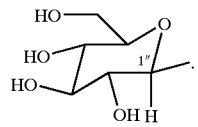

6. The gymnemic acid derivative of claim 1, wherein $R_2$ in formula II is hydrogen, $R_3$ is group of formula:

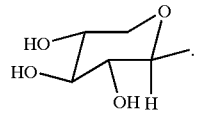

7. The gymnemic acid derivative of claim 1, wherein $R_3$ in formula II is group of formula

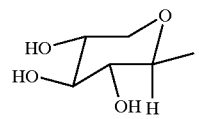

$R_2$ is group of formula:

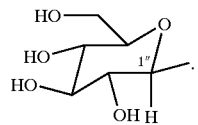

8. A pharmaceutical composition which contains at least one kind of gymnemic acid derivative of formula I and/or II of claim 1 or pharmaceutical base addition salt thereof as active ingredient, a pharmaceutical carrier and an excipient.

9. A composition which contains the gymnemic Acid derivative of formula I and/or II of claim 1, wherein based on the weight of the composition, the amount of compounds A,B,C,D,E and F is 1.25–2.10% compound A, 0.89–1.50% compound B, 2.40–3.80% compound C, 2.10–3.40% compound D, 2.74–4.60% compound E and 3.24–5.40% compound F,
wherein
  A is the gymnemic acid derivative of formula I where $R_1$ is H,
  B is the gymnemic acid derivative of formula I where $R_1$ is the following group

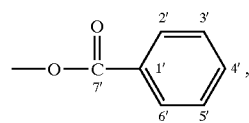

C is the gymnemic acid derivative of formula II where $R_3$ is H and $R_2$ is the following group

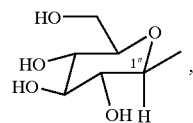

D is the gymnemic acid derivative of formula II where $R_2$ is H and $R_3$ is the following group

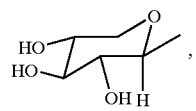

E is the gymnemic acid derivative of formula II where $R_2$ is the following group

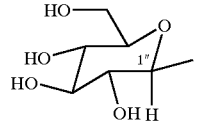

and $R_3$ is the following group

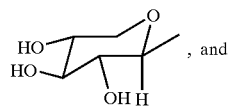, and

F is the gymnemic acid derivative of formula II where $R_3$ is H and $R_2$ is the following group

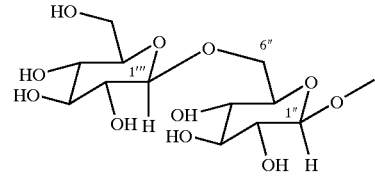

10. An extract of Gymnema sylvestre.R.Br which contains 12.5–40 wt % gymnemic acid derivatives of formula I and formula II of claim 1.

11. A method for the treatment of the diseases and conditions associated with hyperglycemia, hyperlipidemia and platelets aggregation, which comprises:
  administering to a patient in need thereof an effective dose of the gymnemic acid derivative of claim 1 and a pharmaceutically acceptable carrier.

12. A method for the preparation of Gymnemic Acid derivative of formula I and II of claim 1 or a pharmaceutical base addition salt hereof, which includes the following steps:
  a) extracting the plant Gymnema cane with ethanol under reflux and then concentrating;
  b) extracting concentrated liquid in step a) with cyclohexane, then extracting with n-butanol, concentrating to dryness under reduced pressure, and then obtaining a paste;
  c) subjecting the paste in step b) to silica column chromatography with chloroform: methanol=90:10–50:5 or 90:10–60:40 v/v, as elute, obtaining gymnemic acid derivative of formula I and residue;
  d) subjecting the residue in step c) to $C_{18}$ column chromatography with methanol/water 20/80–40/60 v/v as elute, obtaining the gymnemic acid derivative of formula II; and
  e) converting the obtained gymnemic acid derivative of formula I or II into pharmaceutical base addition salt with inorganic or organic base.

13. A composition which contains the gymnemic acid derivative of formula I and/or II of claim 2, wherein based on the weight of the composition, the amount of compounds A,B,C,D,E and F is 1.25–2.10% compound A, 0.89–1.501% compound B, 2.40–3.80% compound C, 2.10–3.40% compound D, 2.74–4.60% compound E and 3.24–5.40% compound F, wherein A is the gymnemic acid derivative of formula I where $R_1$ is H, B is the gymnemic acid derivative of formula I where $R_1$ is the following group

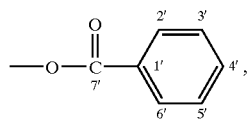

C is the gymnemic acid derivative of formula II where $R_3$ is H and $R_2$ is the following group

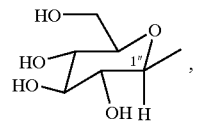

D is the gymnemic acid derivative of formula II where $R_2$ is H and $R_3$ is the following group

E is the gymnemic acid derivative of formula II where $R_2$ is the following group

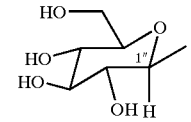

and $R_3$ is the following group

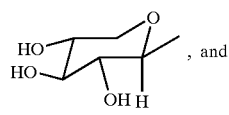

F is the gymnemic acid derivative of formula II where $R_3$ is H and $R_2$ is the following group

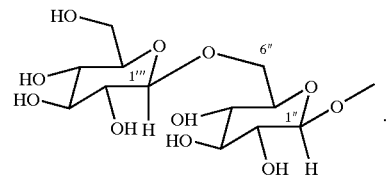.

* * * * *